United States Patent [19]

Köppe et al.

[11] Patent Number: 4,594,344

[45] Date of Patent: Jun. 10, 1986

[54] 1-ARYLOXYPROPANOLAMINES

[75] Inventors: Herbert Köppe, Ingelheim am Rhein; Wolfgang Abele, deceased, late of Waldalgesheim, by Heiderose Schlussas-Abele, legal representative; Franz Esser; Wolfram Gaida, both of Ingelheim am Rhein; Wolfgang Hoefke, Wiesbaden, all of Fed. Rep. of Germany

[73] Assignee: Boehringer Ingelheim KG, Ingelheim am Rhein, Fed. Rep. of Germany

[21] Appl. No.: 755,044

[22] Filed: Jul. 15, 1985

[30] Foreign Application Priority Data

Jul. 25, 1984 [DE] Fed. Rep. of Germany ....... 3427309

[51] Int. Cl.[4] ................. C07D 285/30; C07D 417/12; A61K 31/54
[52] U.S. Cl. ...................................... 514/222; 544/13
[58] Field of Search ........................... 544/13; 514/222

[56] References Cited

U.S. PATENT DOCUMENTS 3,110,716 11/1963 McLamore et al. .................. 544/13

FOREIGN PATENT DOCUMENTS 105732 4/1984 European Pat. Off. .............. 544/13
1470316 4/1969 Fed. Rep. of Germany ........ 544/13

Primary Examiner—John M. Ford

Attorney, Agent, or Firm—Charles J. Herron; David E. Frankhouser; Alan R. Stempel

[57] ABSTRACT

Disclosed are novel compounds having the formula

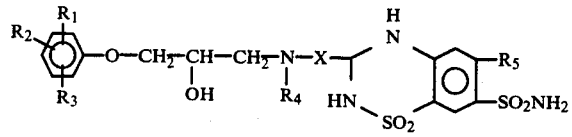

wherein $R_1$ is a hydrogen or halogen atom, a lower alkyl, lower alkoxy, lower alkoxy lower alkyl, lower alkenyl, lower alkenyl oxy, cyano, hydroxy, trifluoromethyl, nitro, amino, aminocarbonylmethyl, lower monoalkylamino, lower dialkylamino group;

$R_2$ is a hydrogen or halogen atom, cyano, lower alkyl or lower alkoxy or acylamino group;

$R_3$ is a hydrogen or halogen atom, a lower alkyl or lower alkoxy group, while $R_2$ and $R_3$ together can also be a butadienyl or methylene dioxy group;

$R_4$ is a hydrogen atom or a lower alkyl group;

$R_5$ is a chlorine atom or a trifluoromethyl group;

X is an alkylene group;

and the non-toxic, pharmaceutically acceptable acid addition salts thereof.

The compounds are suitable for treatment and prophylaxis of hypertension.

31 Claims, No Drawings

1-ARYLOXYPROPANOLAMINES

The invention relates to novel 1-aryloxypropanolamines, their preparation and the use of the novel compounds in therapy, particularly the treatment or prophylaxis of hypertension.

Novel 1-aryloxypropanolamines correspond to formula I:

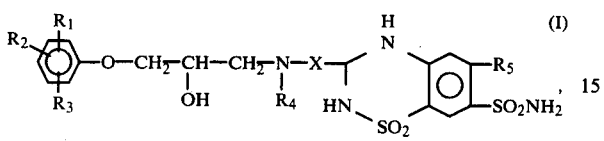

in which $R_1$ is a hydrogen or halogen atom, a lower alkyl, lower alkoxy, lower alkoxy lower alkyl, lower alkenyl, lower alkenyl oxy, cyano, hydroxy, trifluoromethyl, nitro, amino, aminocarbonylmethyl, lower monoalkylamino, lower dialkylamino group;

$R_2$ is a hydrogen or halogen atom, cyano, lower alkyl or lower alkoxy or acylamino group;

$R_3$ is a hydrogen or halogen atom, a lower alkyl or lower alkoxy group, whilst $R_2$ and $R_3$ together can also be a butadienyl or methylene dioxy group;

$R_4$ is a hydrogen atom or a lower alkyl group;

$R_5$ is a chlorine atom or a trifluoromethyl group;

X is an alkylene group;

and the non-toxic, pharmaceutically acceptable acid addition salts thereof.

The term "halogen atoms" is understood to mean in this case fluorine, chlorine and bromine, preference being given to fluorine and more particularly chlorine.

The lower alkyl or lower alkoxy groups contain 1 to 4 and preferably 1 to 3 C-atoms, particular reference being made to groups with 1 to 2 C-atoms. The alkylene group X contains 1 to 8 C-atoms and preferably 1 to 5 C-atoms and more particularly 1 to 3 C-atoms. If the C-chains comprise several C-atoms, they can be branched or unbranched. This also applies to the acyl radical in the acylamino group (definition of $R_2$). The acyl group contains 1 to 8 and preferably 1 to 4 C-atoms and can be aliphatic or aromatic. In the present context, "aromatic radical" is understood to mean a phenyl, monomethyl phenyl or dimethyl phenyl radical, but can also be a benzyl radical.

If the compound of formula I contains several substituents with carbon chains, then the number of carbon atoms in these chains can be the same or different.

The compounds of formula I can be in the form of free bases or acid addition salts. As a result of their asymmetric centers, they can be in the form of racemates or mixtures of enantiomers, or in the form of individual enantiomers.

Suitable processes for the preparation of the novel compound are given hereinafter.

(a) This method comprises reacting a compound of formula II:

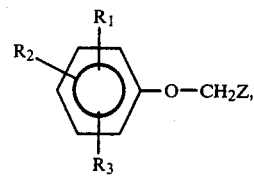

in which $R_1$, $R_2$ and $R_3$ have the above meaning and Z is the group

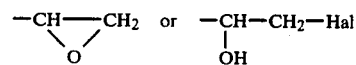

(Hal=halogen, preferably Cl, Br), with a compound of formula III:

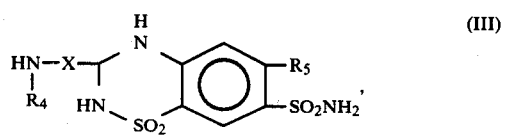

in which $R_4$, $R_5$ and X have the above meanings.

(b) This method comprises reacting a compound of formula IV:

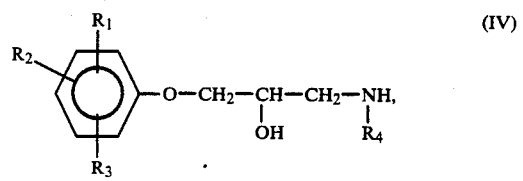

in which $R_1$ to $R_4$ have the above meanings, with a compound of formula V:

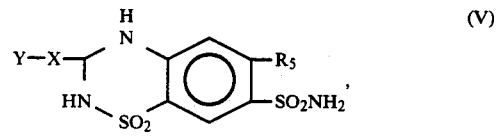

in which $R_5$ and X have the above meanings and Y is an acid residue (e.g., halogen atom, particularly Cl, Br, or sulphonic acid residue) cleavable during the coupling of IV and V, or (c) For the preparation of compounds of formula I in which $R_4$ is a lower alkyl radical, an appropriate method comprises reacting such compounds of formula I in which $R_4$ stands for hydrogen with a compound of formula VI:

in which $R_4$ and Y have the above meanings, and which is suitable for introducing $R_4$=lower alkyl into the amino group.

To the extent that according to processes (a) to (c) initially acid addition salts are obtained, they are converted by conventional methods, if desired, into free bases or into salts of other acids. Initially obtained bases can be optionally converted into acid addition salts.

Process (a) is preferably performed at temperatures between 0° and 40° C., particularly at ambient temperature. The reaction medium consists of alcohols or other polar solvents, e.g., methanol, ethanol, isopropanol, tetrahydrofuran, dioxan, optionally in mixed form.

The acid traps can be tertiary amines (e.g., triethylamine, dimethylaniline, pyridine) or inorganic salts (e.g., $NaHCO_3$, $Na_2CO_3$, $K_2CO_3$) or aqueous bases (e.g., caustic soda solution, caustic potash solution).

Processes (b) and (c) are preferably performed at temperatures between ambient temperature and the boiling temperature of the reaction mixture, particularly at between 40° and 80° C. The reaction medium can be constituted by polar solvents, e.g., dimethyl formamide, tetrahydrofuran, dioxan, methanol, ethanol and propanols. The acid traps are salts such as $NaHCO_3$, $KHCO_3$, $Na_2CO_3$ or tertiary amines.

The starting compounds of formulae II to VI can be prepared by known methods. The compounds according to the invention have two asymmetric C-atoms and therefore occur in the various diastereometric forms.

The 1-aryloxy-3-dihydrobenzothiadiazinyl-alkylamino-2-propanols of formula I according to the invention can be converted in the conventional manner into their non-toxic, pharmaceutically acceptable acid addition salts. Suitable acids are, e.g., hydrochloric, hydrobromic, sulphuric, methane sulphonic, maleic, acetic, oxalic, lactic or tartaric acids.

The compounds of formula I and their non-toxic, pharmaceutically acceptable acid addition salts have revealed valuable therapeutic and in particular hypotensive characteristics in animal tests. They are useful for the treatment or prophylaxis of hypertension in humans and other animals.

Those compounds of formula I in which $R_1$ and $R_2$ are each a chlorine atom, or $R_1$ is a cyano radical in the 2-position and $R_2$ is an acylamino radical in the 4-position, or $R_1$ is an alkoxyalkyl radical in the 4-position have proved to be particularly valuable.

The single dose of the substances according to the invention is 5 to 300 mg, preferably 20 to 150 mg (oral).

The active substances according to the invention can be provided in conventional administration forms, such as tablets, coated tablets, solutions, emulsions, powders, capsules or depot forms. Conventional pharmaceutical adjuvants and conventional production processes can be used for the production thereof. Corresponding tablets can, e.g., be obtained by mixing the active substances with known adjuvants, e.g. inert diluents, such as calcium carbonate, calcium phosphate or lactose, disintegrating agents such as corn starch or alginic acid, binders such as starch or gelatin, lubricants such as magnesium stearate or talc and/or agents for bringing about a depot effect such as carboxypolymethylene, carboxymethylcellulose, cellulose acetate phthalate or polyvinylacetate.

The tablets can also comprise several layers. Thus, coated tablets can be obtained by coating cores similar to those used for plain tablets with agents conventionally used in tablet coatings, e.g. Kollidon or shellac, gum arabic, talc, titanium dioxide or sugar. In order to obtain a depot effect or to avoid incompatibilities the core can also include several layers. Likewise, to obtain a depot effect, the tablet shell can include several layers in which the adjuvants mentioned in connection with the tablets can be used.

Syrups of the active substances or active substance combinations according to the invention can additionally contain a sweetener such as saccharin, cyclamate, glycerol or sugar, together with a taste-improving agent, e.g., flavoring substances such as vanillin or orange extract.

They can also contain suspending aids or thickeners such as sodium carboxymethylcellulose, wetting agents, e.g., condensation products of fatty alcohols with ethylene oxide, or protective agents such as p-hydroxybenzoate.

Injection solutions can be prepared in the conventional manner, e.g., accompanied by the addition of preservatives, such as p-hydroxybenzoates, or stabilizers such as sequestering agents, and they can then be introduced into injection bottles or ampoules.

Capsules containing the active substances or active substance combinations can, e.g. be prepared such that the active substances are mixed with inert carriers such as lactose or sorbitol and are then encapsulated in gelatin capsules.

Suitable suppositories can, e.g., be produced by mixing the active substances or active substance combinations with conventional carriers such as neutral fats or polyethylene glycol, or derivatives thereof.

The compounds according to the invention are also suitable for combination with other active substances such as, e.g., β-adrenolytics, diuretics or tranquilizers.

The following examples illustrate without restricting the invention.

PREPARATION EXAMPLES

Example 1

1-(2,4-dichlorophenoxy)-3-[(6-chloro-7-sulphonamido-1,1-dioxodihydrobenzothiadiazinyl-3)-methylamino]-2-propanol First, 3-aminomethyl-6-chloro-7-sulphonamido-1,1-dioxodihydrobenzothiadiazine-hydrochloride (7.3 g, 0.02 mol) is dissolved in a mixture of ethanol (70 ml) and methanol (30 ml), triethylamine (2 g, 0.02 mol) is added and, accompanied by stirring, 1-(2,4-dichlorophenoxy)-2,3-propyleneoxide (4.4 g, 0.02 mol) is then added. After standing for 48 hours at 20° C., the solvent mixture is distilled off under reduced pressure and the residue left is purified over a silica gel column. Mobile solvent: ethyl acetate (700 parts), isopropanol (300 parts) and ammonia (50 parts). After combining the homogeneous fraction and distilling the solvent mixture, pure substance (7.1 g) was recovered, this was then dissolved in acetonitrile (50 ml). After adding alcoholic HCl, the hydrochloride crystallized in colorless form. After isolation and drying, colorless crystals (2.8 g) were obtained. M.p. 170°–173° C. Following concentration by evaporation, a further 0.7 g of substance crystallized from the mother liquor.

EXAMPLE 2

1-(2-cyanophenoxy)-3-[(6-chloro-7-sulphonamido-1,1-dioxodihydrobenzothiadiazinyl-3)-methylamino]-2-propanol First, 3-aminomethyl-6-chloro-7-sulphonamide-1,1-dioxodihydrobenzothiadiazine-hydrochloride (9 g, 0.03 mol) dissolved in ethanol (80 ml), methanol (20 ml) is added, and this is combined with triethylamine (2.53 g, 0.02 mol).

Then, 1-(2-cyanophenoxy)-2,3-propylene oxide (4.35 g, 0.02 mol) is added at ambient temperature and left to stand for twelve hours. After distilling off the solvent in vacuo, the residue is purified over a silica gel column. Solvent mixture: ethyl acetate (700 parts), isopropanol (300 parts) and ammonia (50 parts). After distilling off the volatile fractions, the combined homogeneous fractions give a base (3.9 g), which is dissolved in ethanol and acidified with ethereal HCl. Following filtration, ether is added up to slight turbidity, after which the substance separates in colorless form. Following suction filtering, the hydrochloride (2.1 g) is obtained. M.p. 170°–172° C.

The compounds of Examples 3 to 14 are synthesized analogously to Example 2.

Example 3

1-[4-(2-methoxyethyl)-phenoxy]-3-[(6-chloro-7-sulphonamido-1,1-dioxodihydrobenzothiadiazinyl-3)-methylamino]-2-propanol-hydrochloride. M.p. 172°–174° C.

Example 4

1-α-naphthoxy-3-[(6-chloro-7-sulphonamido-1,1-dioxodihydrobenzothiadiazinyl-3)-methylamino]-2-propanol-hydrochloride. M.p. 196°–199° C.

Example 5

1-(3-methylphenoxy)-3-[(6-chloro-7-sulphonamido-1,1-dioxodihydrobenzothiadiazinyl-3)-methylamino]-2-propanol-hydrochloride. M.p. 188°–190° C.

Example 6

1-(2-allyloxiphenoxy)-3-[(6-chloro-7-sulphonamido-1,1-dioxodihydrobenzothiadiazinyl-3)-methylamino]-2-propanol-hydrochloride. M.p. 120°–122° C.

Example 7

1-(2-cyano-4-isobutyroylaminophenoxy)-3-[(6-chloro-7-sulphonamido-1,1-dioxydihydrobenzothiadiazinyl-3)-methylamino]-2-propanol-hydrochloride. M.p. 190°–193° C.

Example 8

1-(4-chlorophenoxy)-3-[(6-chloro-7-sulphonamido-1,1-dioxodihydrobenzothiadiazinyl-3)-methylamino]-2-propanol-hydrochloride. M.p. 186°–187° C.

Example 9

1-(2,6-dichlorophenoxy)-3-[(6-chloro-7-sulphonamido-1,1-dioxodihydrobenzothiadiazinyl-3)-methylamino]-2-propanol-hydrochloride. M.p. 184°–186° C.

Example 10

1-(3,4-dichlorophenoxy)-3-[(6-chloro-7-sulphonamido-1,1-dioxodihydrobenzothiadiazinyl-3)-methylamino]-2-propanol-oxalate. M.p. 140°–142° C.

Example 11

1-(3-methoxyphenoxy)-3-[(6-chloro-7-sulphonamido-1,1-dioxodihydrobenzothiadiazinyl-3)-methylamino]-2-propanol-hydrochloride. M.p. 184°–186° C.

Example 12

1-(4-methoxyphenoxy)-3-[(6-chloro-7-sulphonamido-1,1-dioxodihydrobenzothiadiazinyl-3)-methylamino]-2-propanol-hydrochloride. M.p. 188°–189° C.

Example 13

1-(3-trifluoromethylphenoxy)-3-[(6-chloro-7-sulphonamido-1,1-dioxodihydrobenzothiadiazinyl-3)-methylamino]-2-propanol-hydrochloride. M.p. 131°–134° C.

Example 14

1-(3,4-dimethoxyphenoxy)-3-[(6-chloro-7-sulphonamido-1,1-dioxo-dihydrobenzothiadiazinyl-3)-methylamino]-2-propanol-hydrochloride. M.p. 178°–180°.

Example 15

1-(2-cyano-4-isobutyroylamino-phenoxy)-3-N-methyl-3-[6-chloro-7-sulphonamido-1,1-dioxodihydrobenzothiadiazinyl-3)-methylamino]-2-propanol-oxalate First, 3-N-methylaminomethyl-6-chloro-7-sulphonamido-1,1-dioxodihydrobenzothiadiazine-hydrochloride (7.5 g, 0.2 mol) is dissolved in methanol (100 ml), triethyl amine (2.75 ml, 0.02 mol) is added and this is then reacted with 1-(2-cyano-4-isobutyroylaminophenoxy)-2,3-propylene oxide (5.2 g, 0.02 mol) at ambient temperature. After standing for 12 hours, the solvent is distilled in vacuo and the residue is purified over a silica gel column as in Example 2. The thus obtained base is dissolved in acetone and slowly dripped, accompanied by stirring, into a solution of oxalic acid (3.5 g) in acetone (150 ml). After standing ether, the oxalate slowly crystallizes. Following isolation and drying, colorless pure substance (2.8 g) is obtained. M.p. 138°–142° C.

The compounds of Example 16 to 21 are prepared analogously to Example 15.

Example 16

1-(2-cyanophenoxy)-3-N-methyl-3-[(6-chloro-7-sulphonamido-1,1-dioxodihydrobenzothiadiazinyl-3)-methylamino]-2-propanol-oxalate. M.p. 127°–130° C.

Example 17

1-(3,4-dimethoxyphenoxy)-3-N-methyl-3-[(6-chloro-7-sulphonamido-1,1-dioxodihydrobenzothiadiazinyl-3)-methylamino]-2-propanol-oxalate. M.p. 133°–136°0 C.

Example 18

1-(2,4-dichlorophenoxy)-3-N-methyl-3-[(6-chloro-7-sulphonamido-1,1-dioxodihydrobenzothiadiazinyl-3)-methylamino]-2-propanol-hydrochloride. M.p. 174°–177° C.

Example 19

1-(3-methylphenoxy)-3-N-methyl-3-[(6-chloro-7-sulphonamido-1,1-dioxodihydrobenzothiadiazinyl-3)-methylamino]-2-propanol-oxalate. M.p. 143°–146° C.

Example 20

1-(2,4-dichlorophenoxy)-3-N-isopropyl-3-[(6-chloro-7-sulphonamido-1,1-dioxodihydrobenzothiadiazinyl-3)-methylamino]-2-propanol-hydrochloride. M.p. 175°–177° C.

Example 21

1-(2-cyanophenoxy)-3-N-isopropyl-3-[(6-chloro-7-sulphonamido-1,1-dioxodihydrobenzothiadiazinyl-3)-methylamino]-2-propanol-hydrochloride. M.p. 179°–181° C.

Example 22

1-(2-cyanophenoxy)-3-[(6-chloro-7-sulphonamido-1,1-dioxodihydrobenzothiadiazinyl-3)-ethylamino]-2-propanol-hydrochloride.

First, 3-aminoethyl-6-chloro-7-sulphonamido-1,1-dioxodihydrobenzothiadiazine-hydrochloride (7.54 g, 0.02 mol) is dissolved in methanol (100 ml), triethylamine (2.0 g, 0.02 mol is added and then 1-(2-cyanophenoxy)-2,3-propylene oxide (3.5 g, 0.02 mol) is stirred in. After standing for 12 hours at 20° C., the volatile fractions are distilled off in vacuo. The residue is purified over a silica gel column as in Example 2 and the isolated basic fractions are dissolved in acetone. The solution is filtered, acidified with alcoholic hydrochloric acid and left to stand for 20 hours, accompanied by cooling to obtain complete crystallization. The colorless hydrochloride is suction filtered and dried, giving pure substance (1.2 g). M.p. 202°–204° C.

The following compounds are prepared in accordance with Example 22.

Example 23

1-(2,4-dichlorophenoxy)-3-[(6-chloro-7-sulphonamido-1,1-dioxodihydrobenzothiadiazinyl-3)-ethylamino]-2-propanol-hydrochloride. M.p. 187°–190° C.

Example 24

1-(4-methoxyethylphenoxy)-3-[(6-chloro-7-sulphonamido-1,1-dioxodihydrobenzothiadiazinyl-3)ethylamino]-2-propanol-oxalate. M.p. 137°–140° C.

Example 25

1-(3,4-dichlorophenoxy)-3-[(6-chloro-7-sulphonamido-1,1-dioxodihydrobenzothiadiazinyl-3)-ethylamino-]-2-propanol-hydrochloride. M.p. 188°–190° C.

We claim:

1. A compound of formula I:

in which
  $R_1$ is a hydrogen or halogen atom, a lower alkyl, lower alkoxy, lower alkoxy lower alkyl, lower alkenyl, lower alkenyl oxy, cyano, hydroxy, trifluoromethyl, nitro, amino, aminocarbonylmethyl, lower monoalkylamino, lower dialkylamino group;
  $R_2$ is a hydrogen or halogen atom, cyano, lower alkyl or lower alkoxy or acylamino group;
  $R_3$ is a hydrogen or halogen atom, a lower alkyl or lower alkoxy group, whilst $R_2$ and $R_3$ together can also be a butadienyl or methylene dioxy group;
  $R_4$ is a hydrogen atom or a lower alkyl group;
  $R_5$ is a chlorine atom or a trifluoromethyl group;
  X is an alkylene group;
and the non-toxic, pharmaceutically acceptable acid addition salts thereof.

2. A compound of claim 1 in which $R_1$ and $R_2$ are each chlorine atoms.

3. A compound of claim 1 in which $R_1$ is CN in the 2-position and $R_2$ is acylamino in the 4-position.

4. A compound of claim 1 in which $R_1$ is an alkoxy group in the 4-position.

5. A compound of claim 1 which is 1-(2,4-dichlorophenoxy)-3-[(6-chloro-7-sulphonamido-1,1-dioxodihydrobenzothiadiazinyl-3)-methylamino]-2-propanol, or a non-toxic, pharmaceutically acceptable salt thereof.

6. A compound of claim 1 which is 1-(2-cyanophenoxy)-3-[(6-chloro-7-sulphonamido-1,1-dioxodihydrobenzothiadiazinyl-3)-methylamino]-2-propanol, or a non-toxic, pharmaceutically acceptable salt thereof.

7. A compound of claim 1 which is 1-[4-(2-methoxyethyl)-phenoxy]-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

8. A compound of claim 1 which is 1-α-naphthoxy-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

9. A compound of claim 1 which is 1-(3-methylphenoxy)-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

10. A compound of claim 1 which is 1-(2-allyloxiphenoxy)-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

11. A compound of claim 1 which is 1-(2-cyano-4-isobutyroylaminophenoxy)-3-[(6-chloro-7-sulphonamido-1,1-dioxydihydrobenzothiadiazinyl-3)-methylamino]-2-propanol-hydrochloride, or a non-toxic, pharmaceutically acceptable salt thereof.

12. A compound of claim 1 which is 1-(4-chlorophenoxy)-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

13. A compound of claim 1 which is 1-(2,6-dichlorophenoxy)-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

14. A compound of claim 1 which is 1-(3,4-dichlorophenoxy)-3-[(6-chloro-7-sulphonamido-1,1-dioxodihydrobenzothiadiazinyl-3)-methylamino]-2-propanol-oxalate, or a non-toxic, pharmaceutically acceptable salt thereof.

15. A compound of claim 1 which is 1-(3-methoxyphenoxy)-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

16. A compound of claim 1 which is 1-(4-methoxyphenoxy)-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

17. A compound of claim 1 which is 1-(3-trifluoromethylphenoxy)-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

18. A compound of claim 1 which is 1-(3,4-dimethoxyphenoxy)-3-[(6-chloro-7-sulphonamido-1,1-dioxodihydrobenzothiadiazinyl-3)-methylamino]-2-propanolhydrochloride, or a non-toxic, pharmaceutically acceptable salt thereof.

19. A compound of claim 1 which is 1-(2-cyano-4-isobutyroyl-aminophenoxy)-3-N-methyl-3-[6-chloro-7-sulphonamido-1,1-dioxo-dihydrobenzothiadiazinyl-3)-methylamino]-2-propanol-oxalate, or a non-toxic, pharmaceutically acceptable salt thereof.

20. A compound of claim 1 which is 1-(2-cyanophenoxy)-3-N-methyl-3-[(6-chloro-7-sulphonamido-1,1-dioxodihydrobenzothiadiazinyl-3)-methylamino]-2-propanol-oxalate, or a non-toxic, pharmaceutically acceptable salt thereof.

21. A compound of claim 1 which is 1-(3,4-dimethoxyphenoxy)-3-N-methoxy-3-[(6-chloro-7-sulphonamido-1,1-dioxodihydrobenzothiadiazinyl-3)-methylamino]-2-propanol-oxalate, or a non-toxic, pharmaceutically acceptable salt thereof.

22. A compound of claim 1 which is 1-(2,4-dichlorophenoxy)-3-N-methyl-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

23. A compound of claim 1 which is 1-(3-methylphenoxy)-3-N-methyl-3-[(6-chloro-7-sulphonamido-1,1-dioxodihydrobenzothiadiazinyl-3)-methylamino]-2-propanol-oxalate, or a non-toxic, pharmaceutically acceptable salt thereof.

24. A compound of claim 1 which is 1-(2,4-dichlorophenoxy)-3-N-isopropyl-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

25. A compound of claim 1 which is 1-(2-cyanophenoxy)-3-N-isopropyl-3-[(6-chloro-7-sulphonamido-1,1-dioxodihydrobenzothiadiazinyl-3)-methylamino]-2-propanol-hydrochloride, or a non-toxic, pharmaceutically acceptable salt thereof.

26. A compound of claim 1 which is 1-(2-cyanophenoxy)-3-[(6-chloro-7-sulphonamido-1,1-dioxodihydrobenzothiadiazinyl-3)-ethylamino]-2-propanol-hydrochloride, or a non-toxic, pharmaceutically acceptable salt thereof.

27. A compound of claim 1 which is 1-(2,4-dichlorophenoxy)-3-[(6-chloro-7-sulphonamido-1,1-dioxodihydrobenzothiadiazinyl-3)-ethylamino]-2-propanol-hydrochloride, or a non-toxic, pharmaceutically acceptable salt thereof.

28. A compound of claim 1 which is 1-(4-methoxyethylphenoxy)-3-[(6-chloro-7-sulphonamido-1,1-dioxodihydrobenzothiadiazinyl-3)ethylamino]-2-propanol-oxalate, or a non-toxic, pharmaceutically acceptable salt thereof.

29. A compound of claim 1 which is 1-(3,4-dichlorophenoxy)-3-[(6-chloro-7-sulphonamido-1,1-dioxodihydrobenzothiadiazinyl-3)-ethylamino-]-2-propanol-hydrochloride, or a non-toxic, pharmaceutically acceptable salt thereof.

30. A pharmaceutical composition comprising an effective antihypertensive amount of a compound of claim 1 and a non-toxic, pharmaceutically acceptable carrier.

31. A method of treating hypertension in a human or other animal in need thereof, which method comprises administering an effective amount of a compound of claim 1 thereto.

* * * * *